US00PP35574P2

(12) United States Plant Patent
Robb

(10) Patent No.: US PP35,574 P2
(45) Date of Patent: Jan. 9, 2024

(54) ***LAVANDULA* PLANT NAMED 'LAVP1385'**

(50) Latin Name: *Lavandula pedunculata*
Varietal Denomination: LAVP1385

(71) Applicant: Paradise Seed Company Limited, Kulnura (AU)

(72) Inventor: John B. Robb, Kariong (AU)

(73) Assignee: The Paradise Seed Company Limited, Kulnura (AU)

( * ) Notice: Subject to any disclaimer, the term of this patent is extended or adjusted under 35 U.S.C. 154(b) by 0 days.

(21) Appl. No.: 18/184,919

(22) Filed: Mar. 16, 2023

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./445
CPC ..... A01H 5/02
See application file for complete search history.

*Primary Examiner* — Kent L Bell
(74) *Attorney, Agent, or Firm* — Weatherly IP Solutions, LLC; James M. Weatherly

(57) ABSTRACT

A new cultivar of *Lavandula* plant named 'LAVP1385' that is characterized by its low growing dense plant habit and branching, and short peduncles which bear mauve-pink flowers early and repeatedly in the season.

2 Drawing Sheets

Genus and species: *Lavandula pedunculata.*
Variety denomination: 'LAVP1385'.

BACKGROUND

The present invention relates to a new and distinct cultivar of lavender known botanically as *Lavandula pedunculata* and hereinafter referred to by the cultivar name 'LAVP1385'.

'LAVP1385' originates from a *Lavandula* breeding program commenced in 2010 by the inventor in Kulnura, Australia. The aim of the breeding program is to produce new varieties of *Lavandula* which combine free flowering, an upright plant habit, and good heat tolerance.

The inventor developed 'LAVP1385' by controlled open pollination by exposing the inventor's proprietary variety 'Senros' (Australia Plant Breeders Right No. 6430, unpatented in U.S.A.) to pollen available from assembled pollen donor selections including varieties of *Lavandula* previously developed by the inventor but not released or named. The identity of the female parent is *Lavandula pedunculata* 'Senros'. The identity of the male parent is unknown.

After open pollination of the female variety 'Senros', the inventor collected and sowed seeds from 'Senros' and grew the resultant seedlings to maturity. The inventor evaluated the new seedlings for flower bract color and for plant vigor. The inventor selected the instant variety 'LAVP1385' in 2015.

The inventor first asexually propagated 'LAVP1385' in 2015 using semi-ripe vegetative cuttings and has established that 'LAVP1385' reproduces true-to-type in successive asexual propagations.

SUMMARY

The following traits have been repeatedly observed and represent the distinguishing characteristics of the new

*Lavandula* cultivar named 'LAVP1385'. These traits in combination distinguish 'LAVP1385' from all other existing varieties of *Lavandula* known to the inventor. 'LAVP1385' has not been tested under all possible conditions and phenotypic differences may be observed with variations in environmental, climatic, and cultural conditions, without however, any variance in genotype.

1. 'LAVP1385' exhibits a low growing dense plant habit.
2. 'LAVP1385' exhibits short peduncle length.
3. 'LAVP1385' exhibits mid-sized flower spikes which bear mauve-pink colored flowers arranged in vertical rows.
4. 'LAVP1385' exhibits early and repeat flowering.
5. 'LAVP1385' achieves 30 cm in height and width after one year of growth.
6. 'LAVP1385' is 60 cm in height and width at maturity in a large container or planted in the ground.
7. The cultural requirements for 'LAVP1385' are well-draining soil or growing medium, positioning in full sun, and adequate but not excess water.
8. 'LAVP1385' is hardy to USDA Zone 8.

BRIEF DESCRIPTION OF THE PHOTOGRAPHS

Figure 1:
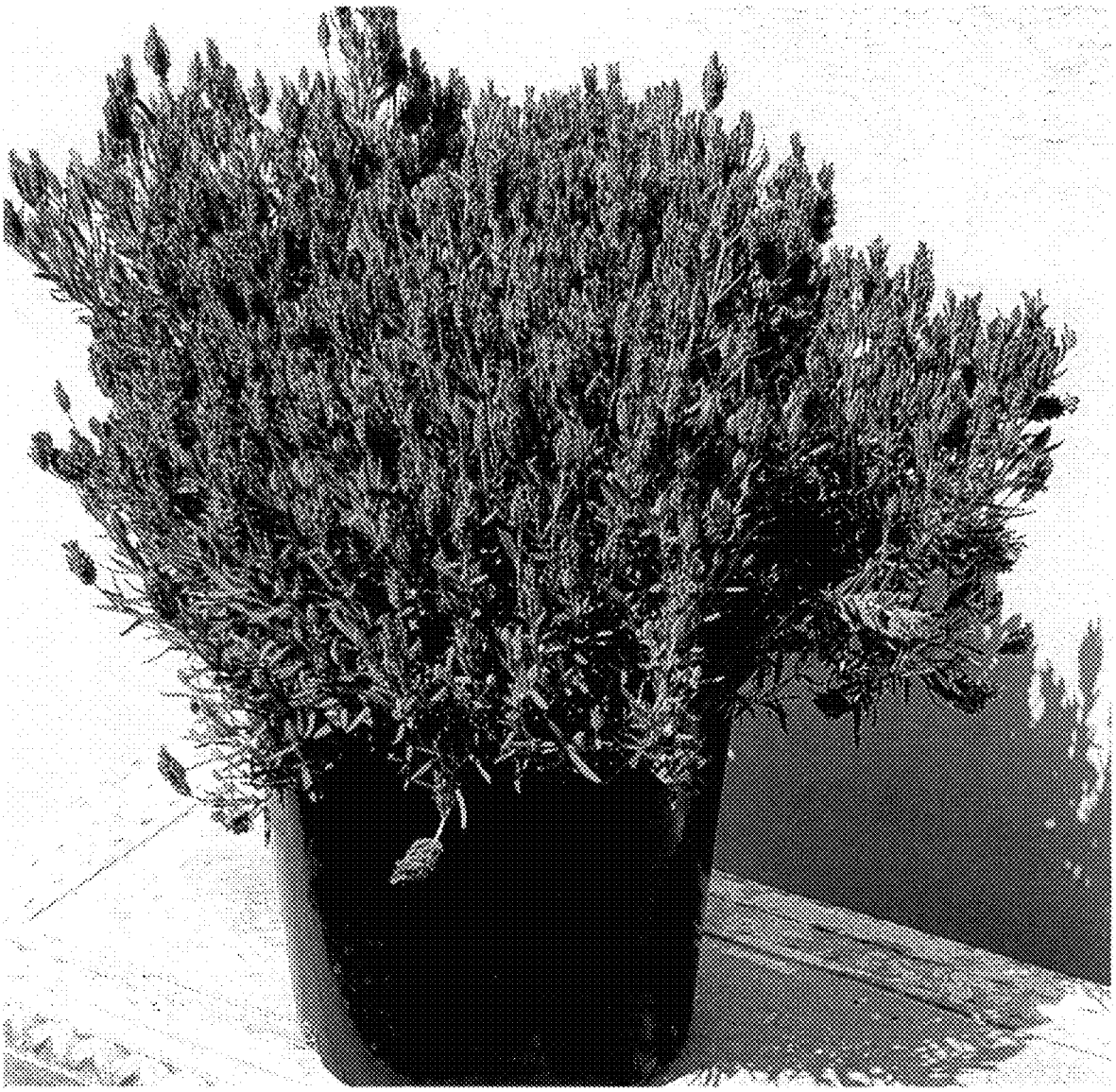
Figure 2:
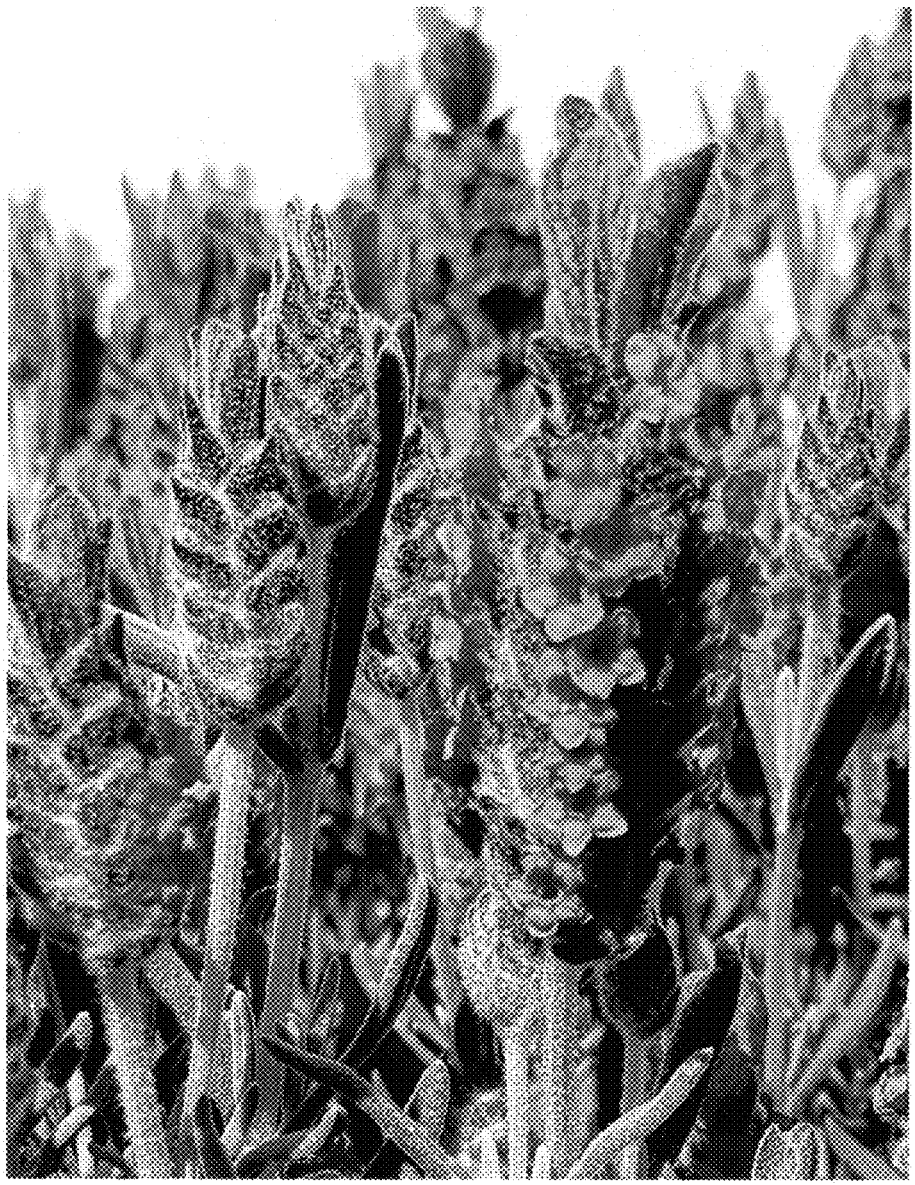

The accompanying photographs labelled FIG. 1 and FIG. 2 illustrate the appearance of 'LAVP1385' showing the colors as true as it is reasonably possible to obtain in color reproductions of this type. Color in the photographs may differ from the color values cited in the detailed botanical description, which accurately describe the actual color of 'LAVP1385'.

FIG. 1 illustrates a two-year-old plant of 'LAVP1385' in full bud and flower in April. The illustrated plant is growing in a 3.7 gallon container in Santa Barbara, Calif.

FIG. 2 presents a close-up view of the inflorescence of 'LAVP1385' which is growing on the mature plant illustrated in FIG. 1.

DESCRIPTION OF THE NEW VARIETY

The following is a detailed botanical description of the *Lavandula* cultivar named 'LAVP1385'. Data was collected in Santa Barbara, Calif. from two-year-old plants grown out of doors in 3.7 gallon containers. Color determinations are made in accordance with The 2007 Royal Horticultural Society Colour Chart of London, England, except where general color terms of ordinary dictionary significance are used. The growing requirements are similar to the species.

Classification:

*Botanical classification.*—*Lavandula pedunculata* 'LAVP1385'.
*Family.*—Lamiaceae.
*Genus.*—*Lavandula.*
*Species.*—*pedunculata.*
*Variety denomination.*—'LAVP1385'.
*Common name.*—Lavender.

Plant:

*Habit.*—Dense.
*Dimensions after one year's growth.*—30 cm in height and width.
*Dimensions at maturity.*—60 cm in height and width.
*Life cycle.*—Perennial.
*Use.*—Ornamental flowering plant for containers or in the landscape.
*Vigor.*—Moderate.
*Hardiness.*—USDA Zone 8.
*Propagation.*—Semi-ripe stem cuttings.
*Root system.*—Fibrous.
*Cultural requirements.*—Full sun, adequate but not excess water, and well-draining soil or growing medium.
*Time to produce a rooted cutting.*—4-6 weeks.
*Time to produce a* 10 *cm container plant in bloom.*—20 weeks.
*Seasonal interest.*—Flower spikes in spring and summer.
*Parentage.*—*Lavandula pedunculata* 'LAVP1385' is a selection that resulted from controlled open pollination of the following parents: Female parent plant: *Lavandula pedunculata* 'Senros' (unpatented). Male parent plant: Unknown selections of *Lavandula pedunculata.*
*Disease susceptibility.*—May be affected by fungal diseases *Botrytis cinerea* and *Anthracnose.*
*Pest susceptibility.*—May be affected by whitefly (*Aleyrodidae*) and mites (*Tetranychidae*).

Stems, branches:

*Number.*—3-5 initial stems arising from first stop or pinch and then approximately 20-25 lateral branches. All branches and stems bear terminal inflorescences.
*Branching habit.*—Erect, less than 30 degrees away from the vertical.
*Stem length* (*to uppermost node*).—18 cm to 22 cm.
*Stem width.*—3 mm.
*Lateral branch length.*—5 cm to 7 cm.
*Lateral branch width.*—2 mm.
*Stem surface* (*older growth*).—Lignified, stiff, rough, glabrous.
*Stem surface* (*new growth and new lateral branch stems*).—Soft, wiry, tomentose.
*Stem color.*—174B (older growth), 138D (new growth and new lateral stems).
*Internode length.*—8 mm to 12 mm.

Foliage:

*Leaf arrangement.*—Opposite.
*Leaf division.*—Simple.
*Leaf shape.*—Narrow lanceolate.
*Leaf margin.*—Entire.
*Leaf apex.*—Acute.
*Leaf base.*—Attenuate.
*Leaf attachment.*—Sessile.
*Leaf color* (*adaxial surface*).—138A.
*Leaf color* (*abaxial surface*).—138B.
*Leaf surface* (*adaxial surfaces*).—Flattened, faintly tomentose.
*Leaf surface* (*abaxial surface*).—Sulcate, veins raised, glabrous.
*Venation.*—Pinnate. Only the mid-vein visible on adaxial surface, all veins visible and raised on abaxial surface.
*Vein color.*—138A (adaxial surface), 138D (abaxial surface).
*Leaf length.*—25 mm to 28 mm.
*Leaf width.*—3.5 mm at widest.
*Leaf fragrance.*—Characteristic resinous lavender scent.

Inflorescence:

*Description.*—Upright cylindrical spike consisting of tubular flowers arranged in eight vertical columns. Each flower is subtended by a basal flower bract and bears 4-6 showy terminal bracts borne at the spike apex.
*Fragrance.*—Characteristic resinous lavender scent.
*Blooming period.*—April through August.
*Inflorescence type.*—Spike.
*Spike length.*—45 mm.
*Spike diameter.*—14 mm-16 mm.
*Spike shape.*—Cylindrical.
*Spike quantity.*—Approximately 300 including buds showing first color.
*Peduncle length.*—38 mm to 50 mm.
*Peduncle width.*—2 mm.
*Peduncle shape.*—Quadrangular, rounded edges.
*Peduncle color.*—138C.
*Peduncle surface.*—Tomentose.
*Tomenta color.*—NN155D.
*Bud* (*immature spike*) *dimensions.*—12 mm-15 mm in length, 7 mm-8 mm in diameter.
*Bud shape.*—Ovoid.
*Bud color.*—138A with longitudinal parallel veins color 138C.
*Bud surface.*—Tomentose, color NN155D.
*Bud apex.*—Acute.

Flowers:

*Description.*—Tubular shape consisting of corolla tube (five fused petals) and five free rotate petal lobes.
*Quantity.*—Approximately 70-75 flowers per individual spike.
*Shape.*—Salverform.
*Corolla tube dimensions.*—5 mm in length, 2.5 mm in diameter.
*Petal lobe shape, dimensions.*—Obovate, 2.5 mm in length, 2 mm in width.
*Petals.*—Five in number, fused except free terminal petal lobes.
*Petal dimensions.*—0.75 mm in length, 1.25 mm in width.
*Petal color* (*both surfaces*).—Ranges between 64B and 72A with darker margins N78A.
*Petal surface* (*both surfaces*).—Glabrous.
*Petal apex* (*of lobes*).—Rounded.
*Petal base.*—Truncate.

*Petal lobe margin*.—Entire.
*Calyx shape*.—Narrow funnel shaped.
*Calyx dimensions*.—3 mm in length, 2 mm diameter.
*Sepals*.—5 in number, fused towards base.
*Sepal dimensions*.—3 mm in length, 1.5 mm in width.
*Sepal color*.—177B.
*Sepal apex*.—Acute.
*Sepal base*.—Truncate.
*Sepal surface* (*both*).—Faintly tomentose.

Basal floral bracts:
*Basal bract shape*.—Deltoid.
*Quantity*.—Approximately 70-75 per spike.
*Basal bract dimensions*.—6 mm in height (base to apex), 7 mm in width.
*Basal bract color*.—137D with longitudinal parallel veins, color N79C.
*Basal bract apex*.—Acute.
*Basal bract base*.—Truncate.
*Basal bract surfaces* (*both surfaces*).—Lanate.
*Basal bract margin*.—Entire.

Terminal bracts:
*Terminal bracts*.—Range of 4 to 6 arising from each spike apex.
*Terminal bract form, shape*.—Petaloid or strap-like.
*Terminal bract surfaces* (*abaxial and adaxial*).—Tomentose.
*Color of hairs*.—155B, down color 155B.
*Terminal bract shape*.—Oblong-obovate.
*Terminal bract margin*.—Combination of sinuous and entire.
*Terminal bract length*.—Range of 1.50 cm. to 2.75 cm.
*Terminal bract width*.—Range of 0.50 cm. to 1 cm.
*Terminal bract apex*.—Rounded.
*Terminal bract base*.—Rounded.
*Terminal bract color* (*adaxial and abaxial surfaces*).—70A or 72A or 72B.
*Vein pattern*.—Reticulate.
*Vein color*.—N77D.

Reproductive organs:
*Stamens*.—Four in number, fine hair-like.
*Filament length*.—1.5 mm-2.0 mm.
*Filament color*.—N78A.
*Anthers*.—Tiny, ellipsoid, less than 0.5 mm in length.
*Anther color*.—155D.
*Pollen*.—None found when plant in full flower.
*Pistil*.—One.
*Style dimensions*.—3 mm in length, less than 0.5 mm in diameter.
*Stigma shape and dimensions*.—Capitate, less than 0.5 mm in diameter.
*Stigma color*.—N78A.
*Ovary*.—Not present.
*Seed*.—None found.

COMPARISON WITH PARENTS

In comparison with the female parent, *Lavandula* 'Senros' and with all of the potential male parents, 'LAVP1385' exhibits darker flower colors, shorter sterile bracts and shorter peduncles.

COMPARISON WITH CLOSEST KNOWN VARIETIES

The varieties of *Lavandula* which the inventor considers most closely to resemble 'LAVP1385' are *Lavandula* 'Boysenberry Ruffles' (U.S. Plant Pat. No. 18,256) and *Lavandula* 'Madrid Pink Improved' (U.S. Plant Pat. No. 14,205).

In comparison with 'Boysenberry Ruffles', 'LAVP1385' exhibits darker colored flowers which are produced earlier in the season.

In comparison with 'Madrid Pink Improved', 'LAVP1385' exhibits darker sterile bracts which are also shorter. In addition, 'LAVP1385' exhibits a more upright growth habit.

I claim:

1. A new and distinct variety of *Lavandula* plant named 'LAVP1385' as described and illustrated herein.

* * * * *